US010385249B2

(12) United States Patent
Bulinski et al.

(10) Patent No.: US 10,385,249 B2
(45) Date of Patent: Aug. 20, 2019

(54) HYDROFLUOROETHER OLEFINS AND METHODS OF USING SAME

(71) Applicant: 3M INNOVATIVE PROPERTIES COMPANY, St. Paul, MN (US)

(72) Inventors: Michael J. Bulinski, Stillwater, MN (US); Michael G. Costello, Afton, MN (US); William M. Lamanna, Stillwater, MN (US); Georgiy Teverovskiy, St. Louis Park, MN (US); Kiah A. Smith, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/012,811

(22) Filed: Jun. 20, 2018

(65) Prior Publication Data

US 2018/0298262 A1 Oct. 18, 2018

Related U.S. Application Data

(63) Continuation of application No. 15/326,170, filed as application No. PCT/US2015/040684 on Jul. 16, 2015, now Pat. No. 10,030,185.

(60) Provisional application No. 62/025,152, filed on Jul. 16, 2014.

(51) Int. Cl.
| | | |
|---|---|---|
| *C07D 413/12* | (2006.01) |
| *C07D 265/30* | (2006.01) |
| *C09K 5/10* | (2006.01) |
| *C09K 5/04* | (2006.01) |
| *C07C 211/24* | (2006.01) |
| *H01F 27/18* | (2006.01) |
| *H01L 23/427* | (2006.01) |
| *H01L 21/67* | (2006.01) |
| *H05K 1/02* | (2006.01) |
| *H05K 7/20* | (2006.01) |

(52) U.S. Cl.
CPC .............. *C09K 5/10* (2013.01); *C07C 211/24* (2013.01); *C07D 265/30* (2013.01); *C07D 413/12* (2013.01); *C09K 5/04* (2013.01); *H01F 27/18* (2013.01); *H01L 21/67098* (2013.01); *H01L 23/427* (2013.01); *H05K 1/0203* (2013.01); *H05K 7/2029* (2013.01)

(58) Field of Classification Search
CPC .......... C09K 5/10; C09K 5/04; C07C 211/24; C07D 265/30; C07D 413/12; H01F 27/18; H01L 21/27098; H01L 23/427; H05K 1/0203; H05K 7/2029
See application file for complete search history.

(56) References Cited

U.S. PATENT DOCUMENTS

| | | |
|---|---|---|
| 2,713,593 A | 7/1955 | Brice |
| 4,788,339 A | 11/1988 | Moore |
| 4,985,556 A | 1/1991 | Abe |
| 6,203,944 B1 | 3/2001 | Turner |
| 6,303,080 B1 | 10/2001 | Tuma |
| 2007/0001814 A1 | 1/2007 | Steinke |
| 2007/0018134 A1 | 1/2007 | Costello |
| 2008/0139683 A1 | 6/2008 | Flynn |
| 2010/0139274 A1 | 6/2010 | Zyhowski |
| 2010/0263885 A1 | 10/2010 | Tuma |
| 2011/0100601 A1 | 5/2011 | Flynn |
| 2011/0282104 A1 | 11/2011 | Bartelt |

FOREIGN PATENT DOCUMENTS

| | | |
|---|---|---|
| DE | 283994 | 10/1990 |
| WO | WO 1996-22356 | 4/1996 |
| WO | WO 1999-19707 | 4/1999 |
| WO | WO 2000-03444 | 1/2000 |
| WO | WO 2001-27217 | 4/2001 |
| WO | WO 2010-094019 | 8/2010 |

OTHER PUBLICATIONS

Banks, "Preparation, Properties and Industrial Applications of Organofluorine Compounds", 19-43 (1982).
Ellis, "Cleaning and Contamination of Electronics Components and Assemblies" 182-195 (1986).
Kurykin, "Reaction of trans-Perfluro-2-Pentene With Alcholates", 1982, pp. 2203-2206. [Translated from Izvestiya Akademii Nauk SSSR, Seriya Khimicheskaya, Nov. 1981, No. 11, pp. 2647-2650.]
Vij, "Perfluorovinyl Morpholine and Perfluorovinyl Pyrrolidine with Nucleophiles and Elecrophiles", Z anorg allg. Chem., 1995, pp. 1865-1874.
Wenjuan, "Studies on Electrochemical Fluorination", 1987, vol. 2, pp. 133-137.
Extended Search Report, EP15821640, dated Feb. 5, 2018, 6 pages.
International Search Report for PCT International Application No. PCT/US15/40684 dated Oct. 16, 2015, 3 pages.

*Primary Examiner* — Rebecca L Anderson
(74) *Attorney, Agent, or Firm* — Adam Bramwell

(57) ABSTRACT

A hydrofluoroether compound represented by the following general formula:

$$\begin{array}{c} Rf_5 \\ \phantom{Rf}\diagdown \\ \phantom{Rf}N-C=C \\ Rf_6 \phantom{\diagdown} | \phantom{\diagup} \diagdown \\ \phantom{RfRfRf}Rf_7 \phantom{RfRf} O-Rfh_1-O \end{array} \begin{array}{c} Rf'_8 \phantom{RfRf} Rf'_7 \phantom{Rf} Rf_5 \\ \diagdown \phantom{Rf} | \phantom{Rf} \diagup \\ C=C-N \\ \diagup \phantom{Rfabcde} \diagdown \\ \phantom{RfRfRf} Rf_6 \end{array}$$

5 Claims, No Drawings

HYDROFLUOROETHER OLEFINS AND METHODS OF USING SAME

CROSS REFERENCE TO RELATED APPLICATIONS

This application is a continuation of U.S. application Ser. No. 15/326,170, filed Jan. 13, 2017, now allowed, which is a national stage filing under 35 U.S.C. 371 of PCT/US2015/040684, filed Jul. 16, 2015, which claims the benefit of U.S. Application No. 62/025,152, filed Jul. 16, 2014, the disclosure of which is incorporated by reference in their entirety herein.

FIELD

The present disclosure relates to working fluids that contain hydrofluoroether olefins and methods of making and using the same.

BACKGROUND

Various hydrofluoroether olefin compounds are described in, for example PCT Published Application WO 2010/094019 (Bartelt et al.), and Reaction of Trans-perfluoropent-2-ene with alcoholates, Kurykin, M. A., German, L. S. Izvestiya Akademii Nauk SSSR, Seriya Khimicheskaya (1981), (11), 2647-50.

SUMMARY

In some embodiments, a hydrofluoroether compound represented by the following general formula (I) is provided.

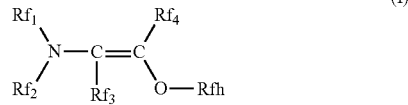

(i) $Rf_3$ is F, $Rf_4$ is $CF_3$, and $Rf_1$ and $Rf_2$ are independently perfluoroalkyl groups (a) having 1 to 2 carbon atoms and optionally comprising at least one catenated heteroatom, or (b) that are bonded together to form a ring structure having 4-8 carbon atoms and optionally comprising one or more catenated heteroatoms; or (ii) $Rf_3$ is $CF_3$, $Rf_4$ is F, and $Rf_1$ and $Rf_2$ are independently perfluoroalkyl groups (a) having 1 to 8 carbon atoms and optionally comprising at least one catenated heteroatom, or (b) that are bonded together to form a ring structure having 4 to 8 carbon atoms and optionally comprising one or more catenated heteroatoms. Rfh is a linear, branched, or cyclic alkyl or fluoroalkyl group of from 1 to 10 carbon atoms that may be saturated or unsaturated and optionally comprises one or more catenated heteroatoms.

In some embodiments, a hydrofluoroether compound represented by the following general formula (II) is provided.

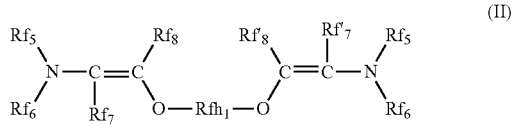

$Rf_5$ and $Rf_6$ (i) are each independently perfluoroalkyl groups having 1-8 carbon atoms and optionally comprising at least one catenated heteroatom, or (ii) are bonded together to form a ring structure having 4-8 carbon atoms and optionally comprising one or more catenated heteroatoms. $Rfh_1$ is a linear, branched, cyclic, or acyclic alkylene or fluoroalkylene group having from 1 to 8 carbon atoms and optionally comprising one or more catenated heteroatoms. Each of $Rf_7$, $Rf_8$, $Rf'_7$, and $Rf'_8$ is independently a F or $CF_3$ group, with the proviso that when: $Rf_7$ is F, $Rf_8$ is $CF_3$, $Rf'_8$ is F, $Rf'_7$ is $CF_3$, $Rf'_7$ is F, $Rf'_8$ is $CF_3$, $Rf'_8$ is F, $Rf'_7$ is $CF_3$.

In some embodiments, an apparatus for heat transfer is provided. The apparatus includes a device and a a mechanism for transferring heat to or from the device. The mechanism comprises a heat transfer fluid that comprises a hydrofluoroether compound as described above.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

In view of an increasing demand for environmentally friendly and lox toxicity chemical compounds, it is recognized that there exists an ongoing need for new working fluids exhibiting further reductions in environmental impact and toxicity, and which can meet the performance requirements of a variety of different applications, and be manufactured cost-effectively.

As used herein, "catenated heteroatom" means an atom other than carbon (for example, oxygen, nitrogen, or sulfur) that is bonded to at least two carbon atoms in a carbon chain (linear or branched or within a ring) so as to form a carbon-heteroatom-carbon linkage.

As used herein, "fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

As used herein, "substituted" (in reference to a group or moiety) means that at least one carbon-bonded hydrogen atom is replaced with a halogen atom. Halogen atoms may include F, Cl, Br, and I.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to hydrofluoroether olefin compounds represented by the following general formula (I):

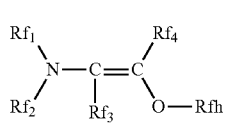
(I)

In various embodiments, $Rf_3$ is F, $Rf_4$ is $CF_3$, and $Rf_1$ and $Rf_2$ are independently perfluoroalkyl groups (i) having 1 to 2, 1 or 2 carbon atoms and optionally comprising at least one catenated heteroatom, or (ii) that are bonded together to form a ring structure having 4-8 or 4 to 6 carbon atoms and optionally comprising one or more catenated heteroatoms. In some embodiments, the catenated hereteroatoms of the ring structure are selected from oxygen, nitrogen or sulfur In some embodiments, $Rf_3$ is $CF_3$, $Rf_4$ is F, and $Rf1$ and $Rf_2$ are independently perfluoroalkyl groups (i) having 1 to 8, 1 to 6, or 2 to 5 carbon atoms and optionally comprising at least one catenated heteroatom, or (ii) that are bonded together to form a ring structure having 4 to 8 or 4 to 6 carbon atoms and optionally comprising one or more catenated heteroatoms selected from oxygen, nitrogen or sulfur. In some embodiments, the catenated hereteroatoms of the ring structure are selected from oxygen and nitrogen.

In some embodiments, Rfh is a linear or branched, cyclic or acyclic, substituted or unsubstituted, monovalent alkyl or fluoroalkyl group of from 1 to 10, 1 to 6, or 1 to 3 carbon atoms that may be saturated or unsaturated and optionally can contain one or more catenated heteroatoms.

In some embodiments, the present disclosure is directed to hydrofluoroether olefin compounds represented by the following general formula (II):
(II)

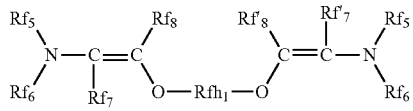

In various embodiments, each $Rf_5$ and $Rf_6$ is independently a perfluoroalkyl group having 1 to 8, 1 to 6, or 2 to 5 carbon atoms and optionally comprises at least one catenated heteroatom. In other embodiments, adjacent $Rf_5$ and $Rf_6$ groups are bonded together to form a ring structure having 4 to 8 or 4 to 6 carbon atoms and optionally comprising one or more catenated heteroatoms. In some embodiments, the catenated hereteroatoms of the ring structure are selected from oxygen and nitrogen. Each of $Rf_7$, $Rf_8$, $Rf'_7$, and $Rf'_8$ is independently a F or $CF_3$ group, with the proviso that when:

$Rf_7$ is F, $Rf_8$ is $CF_3$,
$Rf_8$ is F, $Rf_7$ is $CF_3$,
$Rf'_7$ is F, $Rf'_8$ is $CF_3$, $Rf'_8$ is F, $Rf'_7$ is $CF_3$.

In various embodiments, $Rfh_1$ is a linear or branched, cyclic or acyclic, substituted or unsubstituted, divalent alkylene or fluoroalkylene group having from 1 to 8, 2 to 6, or 2 to 4 carbon atoms that is saturated or unsaturated and optionally comprises one or more catenated heteroatoms.

In some embodiments, the Rfh groups may include: $-CH_3$, $-C_2H_5$, $-C_3H_7$, $-CH_2CH=CH_2$, $CH_2CCH$, $-CH_2CH_2OCH_3$, $-CH_2CF_3$, $-CH_2C_2F_5$, $-CH(CF_3)_2$, $-CH_2C_3F_7$, $-CH_2CF_2CFHCF_3$, $-CH(CH_3)CF_2CFHCF_3$, $-CH_2(CF_2CF_2)_nH$ (where n=1-3), $-CH_2CH_2(CF_2)_xF$ (where x=1-8), and

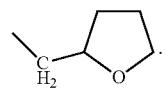

In various embodiments, $Rfh_1$ groups may include: $-CH_2CF_2CF_2CH_2-$, $-CH_2CH_2CH_2CH_2-$, $-CH_2CH=CHCH_2-$, and $-CH_2CH_2OCH_2CH_2-$. The hydrogen atoms in Rfh and $Rfh_1$ can be partially substituted with halogen atoms. The halogen atoms may include F, Cl, Br, and I, but are preferably F or Cl, most preferably F. In some embodiments, the halogen content in the compounds of general formula (I) and (II) may be sufficient to make the hydrofluoroether non-flammable according to ASTM D-3278-96 e-1 test method ("Flash Point of Liquids by Small Scale Closed Cup Apparatus").

In some embodiments, any of the above discussed O heteroatoms may be secondary O heteroatoms wherein the O is bonded to two carbon atoms. In some embodiments, any of the above discussed N heteroatoms may be tertiary N heteroatoms wherein the N is bonded to three perfluorinated carbon atoms. In some embodiments, any of the above discussed S catenated heteroatoms may be secondary S heteroatoms wherein the S is bonded to two perfluorinated carbon atoms, and the remaining valences on S, if present, are occupied by F.

For purposes of the present disclosure, it is to be appreciated that the hydrofluoroether olefin compounds may include the cis isomer, the trans isomer, or a mixture of the cis and trans isomers, irrespective of what is depicted in a general formula.

In various embodiments, representative examples of the compounds of general formula (I) include the following:

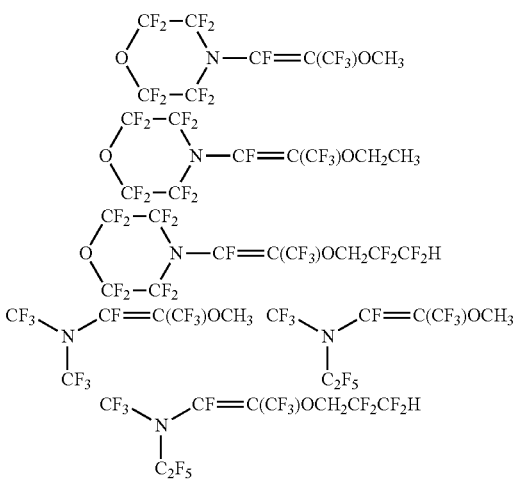

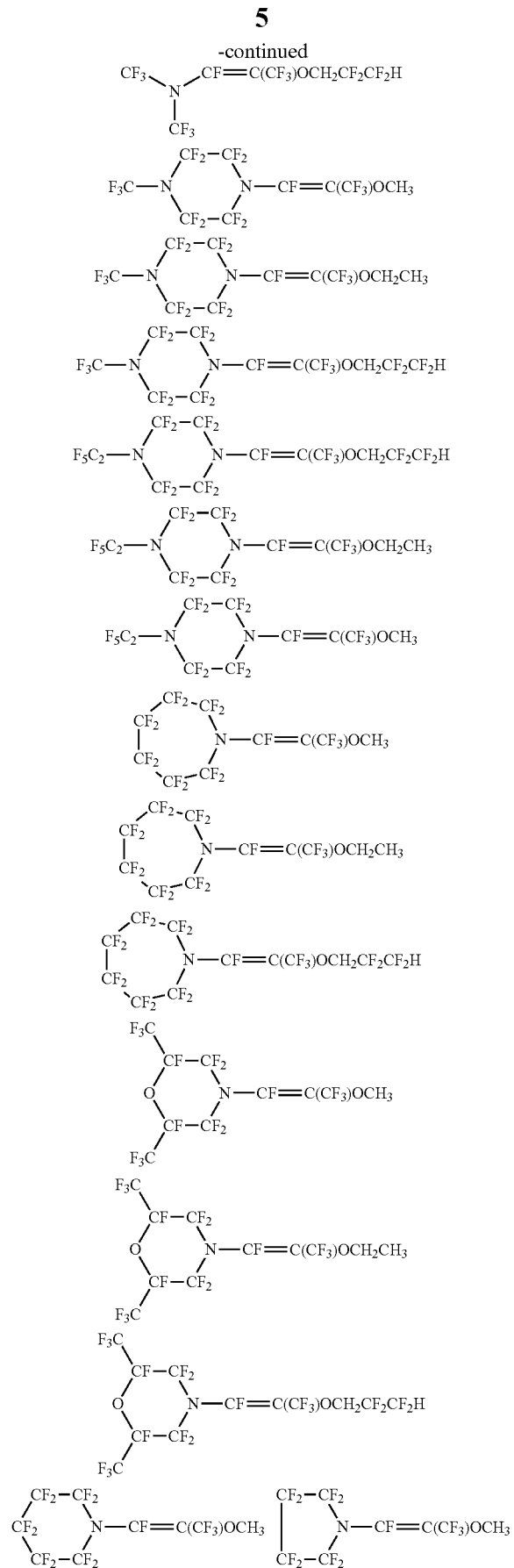

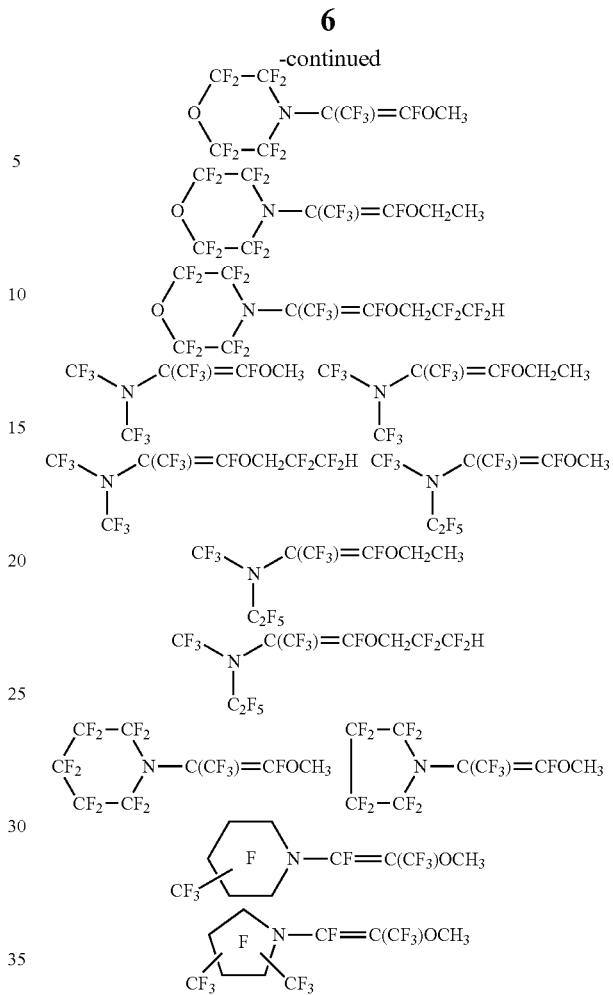

In illustrative embodiments, representative examples of the compounds of general formula (II) include the following:

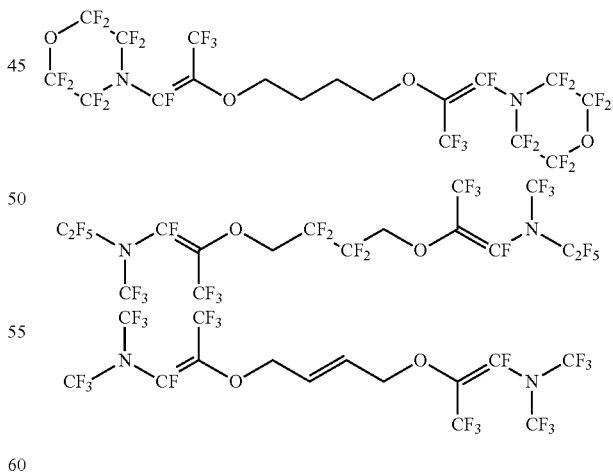

In some embodiments, the hydrofluoroether olefin compounds of the present disclosure may be hydrophobic, relatively chemically unreactive, and thermally stable. The hydrofluoroether olefin compounds may have a low environmental impact. In this regard, the hydrofluoroether olefin compounds of the present disclosure may have a global warming potential (GWP) of less 300, 200, 100 or even less than 10. As used herein, GWP is a relative measure of the warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i [C(t)] dt}{\int_0^{ITH} a_{CO_2} [C_{CO_2}(t)] dt} = \frac{\int_0^{ITH} a_i C_{oi} e^{-t/\tau} dt}{\int_0^{ITH} a_{CO_2} [C_{CO_2}(t)] dt}$$

In this equation a, is the radiative forcing per unit mass increase of a compound in the atmosphere (the change in the flux of radiation through the atmosphere due to the IR absorbance of that compound), C is the atmospheric concentration of a compound, τ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the hydrofluoroether olefin compounds of the present disclosure can be prepared by electrochemically fluorinating a methyl ester to produce the perfluorinated acyl fluoride. The methyl esters can be prepared by well known methods in the literature such as the Michael reaction of an amine with an alkene such as methyl methacrylate. Once prepared these organics can be made to undergo electrochemical fluorination by the method described in, for example, U.S. Pat. No. 2,713,593 (Brice et al.) and in R. E. Banks, Preparation, Properties and Industrial Applications of Organofluorine Compounds, pages 19-43, Halsted Press, New York (1982)). Upon isolation, these acid fluorides can be reacted with metal carbonate salts such as potassium carbonate and sodium carbonate at elevated temperatures to produce the intermediate perfluoroolefins (i.e., perfluorinated propenyl amines). These intermediate perfluoroolefins can then be reacted with various hydrocarbon or fluorinated alcohols in the presence of a base and optionally an organic solvent to produce the compounds of the present disclosure.

The nitrogen-containing hydrofluoroether olefin of the present disclosure can be conveniently prepared in high yield by the addition of an alcohol to a perfluorinated propenyl amine in the presence of a suitable base, as illustrated in Scheme 1.

Scheme 1:

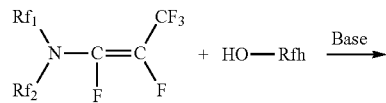

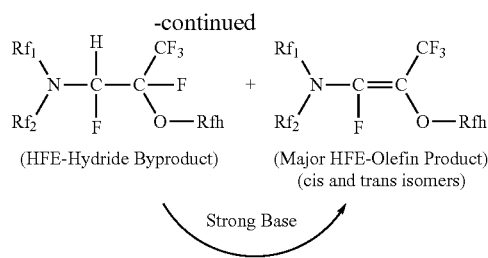

(HFE-Hydride Byproduct)   (Major HFE-Olefin Product)
                          (cis and trans isomers)

Strong Base

Generally this reaction produces the desired hydrofluoroether (HFE) olefin of the present disclosure as the major product, although relatively small amounts of the corresponding HFE-Hydride byproduct can be produced as well. The HFE-Hydride byproduct, if formed, is readily converted to the desired HFE-Olefin by post-treatment with a strong base, such as KOH or a salt of t-butoxide, ultimately producing high yields of the desired and relatively pure HFE-Olefin product.

The alcohol addition reaction illustrated in Scheme 1 can be effected by combining the perfluorinated propenyl amine starting compound and the starting alcohol in the presence of at least one base (for example, a Lewis base). Useful bases include potassium carbonate, cesium carbonate, potassium fluoride, potassium hydroxide, potassium methoxide, triethylamine, trimethylamine, potassium cyanate, potassium bicarbonate, sodium carbonate, sodium bicarbonate, sodium methoxide, cesium fluoride, lithium t-butoxide, potassium t-butoxide, and the like, and mixtures thereof; with potassium carbonate, potassium hydroxide, and mixtures thereof being preferred. A metal salt of the starting alcohol reagent can also be used as the base.

The reactants and base can be combined in a reactor (for example, a glass reactor or a metal pressure reactor) in any order, and the reaction can be run at a desired temperature (for example, from about 0° C. to about 75° C.) under the above described conditions with agitation. Generally, however, use of a non-reactive, aprotic organic solvent (for example, acetonitrile, acetone, tetrahydrofuran, glyme, or a mixture of two or more thereof) can facilitate the reaction. The resulting product can be purified by, for example, distillation. HFE-Hydride reaction by-products can be removed (or converted to desired product) by reaction with a strong base or a good HF scavenger that will preferentially dehydrofluorinate the HFE-Hydride. Strong bases suitable for this purpose include, for example, potassium hydroxide, potassium t-butoxide, lithium t-butoxide, lithium diisopropylamide, DBU and the like. These bases can be used with or without a solvent or a phase transfer catalyst.

The perfluorinated propenyl amine starting compounds can be prepared by standard synthetic procedures that are well known in the art, including those described by Abe in JP 01070444A and JP 0107445A, which are incorporated herein by reference in their entirety.

Representative examples of perfluorinated propenyl amines useful as starting compounds for preparing the nitrogen-containing HFE-Olefin compositions of this disclosure include, for example, 1- and 2-propenyl amines, shown in FIGS. 1 and 2, respectively. Although the structures in FIG. 1 are all shown as trans isomers, the corresponding cis isomers are equally useful starting compounds. Typically the cis and trans perfluorinated 1-propenyl amine starting compounds of FIG. 1 are made and used as a mixture of cis and trans isomers.

FIG. 1: Perfluorinated 1-Propenyl Amines

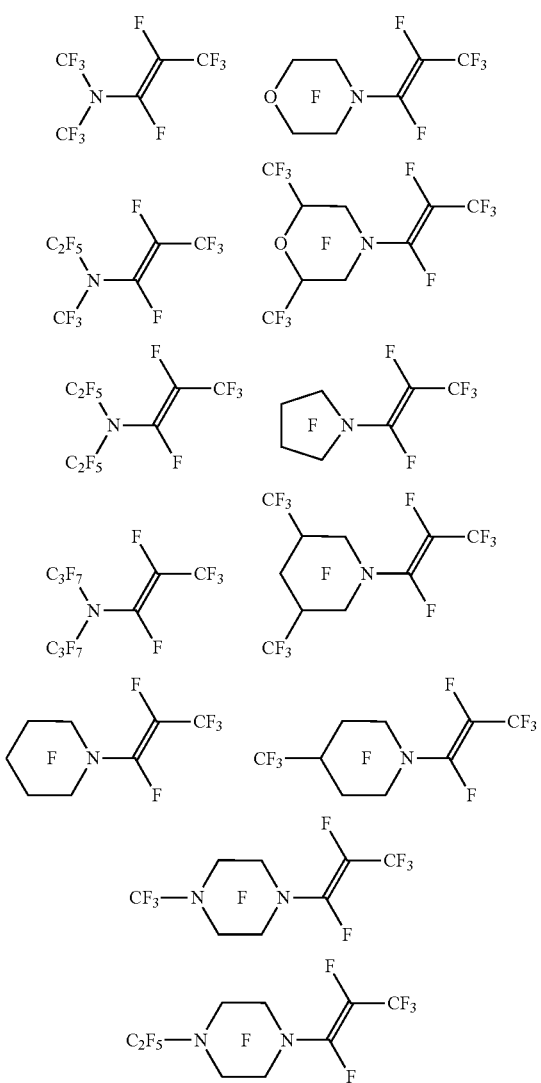

Note: The 1-propenyl amines in FIG. 1, above, can be cis or trans isomers or a mixture thereof, although only the trans isomers are shown.

FIG. 2: Perfluorinated 2-Propenyl Amines

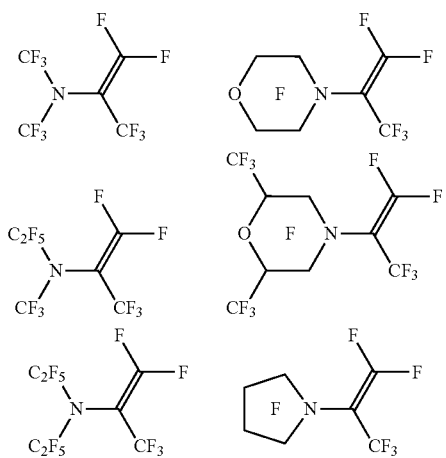

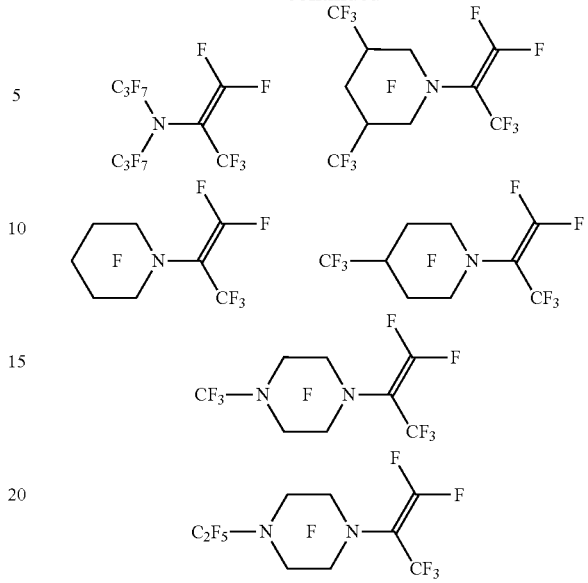

Alcohols useful as starting compounds for preparing the HFE-Olefin compositions of this disclosure can be monofunctional or polyfunctional alcohols. In one embodiment the alcohols are monofunctional. In another embodiment, the alcohols are difunctional.

Useful alcohols are generally commercially available or readily prepared and provide the desired HFE-Olefin product in high yield. In some embodiments, hydrocarbon alcohols may be employed due to their relatively lower cost (in comparison with fluorocarbon alcohols). In some embodiments, suitable alcohols are generally those that provide HFE-Olefin products that are non-flammable. In this regard, mono-functional hydrocarbon alcohols having no more than six carbon atoms or three carbon atoms may be useful.

Representative examples of suitable alcohols include, for example, methanol, ethanol, propanol, butanol, 2-methoxyethanol, tetrahydrofurfuryl alcohol, 1,4-butanediol, 2-butene-1,4-diol, diethyleneglycol, $(CH_3)_2NC_2H_4OH$, $CF_3CH_2OH$, $C_2F_5CH_2OH$, $C_3F_7CH_2OH$, $(CF_3)_2CHOH$, $HCF_2CF_2CH_2OH$, $H(CF_2CF_2)_2CH_2OH$, $H(CF_2CF_2)_3CH_2OH$, $CF_3CFHCF_2CH_2OH$, $CF_3CFHCF_2CH(CH_3)OH$, $C_4F_9CH_2CH_2OH$, $C_6F_{13}CH_2CH_2OH$, $C_8F_{17}CH_2CH_2OH$, $C_4F_9OCH_2CH_2OH$, $HOCH_2CF_2CF_2CH_2OH$, or the like.

In some embodiments, the alcohols include methanol, ethanol, 1-propanol, 2-methoxyethanol, 1,4-butanediol, 2-butene-1,4-diol, diethylene glycol, $CF_3CH_2OH$, $HCF_2CF_2CH_2OH$, $H(CF_2CF_2)_2CH_2OH$, $CF_3CFHCF_2CH_2OH$, $CF_3CFHCF_2CH(CH_3)OH$, $C_4F_9CH_2CH_2OH$ and $HOCH_2CF_2CF_2CH_2OH$.

In some embodiments, the present disclosure is further directed to working fluids that include the above-described hydrofluoroether compounds as a major component. For example, the working fluids may include at least 25%, at least 50%, at least 70%, at least 80%, at least 90%, at least 95%, or at least 99% by weight of the above-described hydrofluoroether compounds based on the total weight of the working fluid. In addition to the hydrofluoroether compounds, the working fluids may include a total of up to 75%, up to 50%, up to 30%, up to 20%, up to 10%, or up to 5% by weight of one or more of the following components: alcohols, ethers, alkanes, alkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrofluoroolefins, hydrochlorofluoroolefins, hydrofluoroethers, or mixtures thereof, based on the total weight of the working fluid. Such additional components can be chosen to modify or enhance the properties of a composition for a particular use.

In some embodiments, the present disclosure is further directed to an apparatus for heat transfer that includes a device and a mechanism for transferring heat to or from the device. The mechanism for transferring heat may include a heat transfer working fluid that includes a hydrofluoroether compound of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more hydrofluoroether compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In some embodiments, the present disclosure is directed to a fire extinguishing composition. The composition may include one or more hydrofluoroether compound of the present disclosure and one or more co-extinguishing agents.

In illustrative embodiments, the co-extinguishing agent may include hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, hydrobromocarbons, iodofluorocarbons, fluorinated ketones, hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, unsaturated fluoro-ethers, bromofluoroolefins, chlorofluorolefins, iodofluoroolefins, fluorinated vinyl amines, fluorinated aminopropenes and mixtures thereof.

Such co-extinguishing agents can be chosen to enhance the extinguishing capabilities or modify the physical properties (e.g., modify the rate of introduction by serving as a propellant) of an extinguishing composition for a particular type (or size or location) of fire and can preferably be utilized in ratios (of co-extinguishing agent to hydrofluoroether compound) such that the resulting composition does not form flammable mixtures in air.

In some embodiments, the hydrofluoroether compounds and the co-extinguishing agent may be present in the fire extinguishing composition in amounts sufficient to suppress or extinguish a fire. The hydrofluoroether compounds and the co-extinguishing agent can be in a weight ratio of from about 9:1 to about 1:9.

In some embodiments, the present disclosure is directed to an apparatus for converting thermal energy into mechanical energy in a Rankine cycle. The apparatus may include a working fluid that includes one or more hydrofluoroether compounds of the present disclosure. The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more hydrofluoroether compounds of the present disclosure to form a vaporized working fluid. In some embodiments, the heat is transferred from the heat source to the working fluid in an evaporator or boiler. The vaporized working fluid may pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.). The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

The present disclosure relates to the use of the hydrofluoroether compounds of the present disclosure as nucleating agents in the production of polymeric foams and in particular in the production of polyurethane foams and phenolic foams. In this regard, in some embodiments, the present disclosure is directed to a foamable composition that includes one or more blowing agents, one or more foamable polymers or precursor compositions thereof, and one or more nucleating agents that include a hydrofluoroether compound of the present disclosure.

In some embodiments, a variety of blowing agents may be used in the provided foamable compositions including liquid or gaseous blowing agents that are vaporized in order to foam the polymer or gaseous blowing agents that are generated in situ in order to foam the polymer. Illustrative examples of blowing agents include hydrochlorofluorocarbons (HCFCs), hydrofluorocarbons (HFCs), hydrochlorocarbons (HCCs), iodofluorocarbons (IFCs), hydrocarbons, hydrofluoroolefins (HFOs) and hydrofluoroethers (HFEs). The blowing agent for use in the provided foamable compositions can have a boiling point of from about −45° C. to about 100° C. at atmospheric pressure. Typically, at atmospheric pressure the blowing agent has a boiling point of at least about 15° C., more typically between about 20° C. and about 80° C. The blowing agent can have a boiling point of between about 30° C. and about 65° C. Further illustrative examples of blowing agents that can be used in the invention include aliphatic and cycloaliphatic hydrocarbons having about 5 to about 7 carbon atoms, such as n-pentane and cyclopentane, esters such as methyl formate, HFCs such as $CF_3CF_2CHFCHFCF_3$, $CF_3CH_2CF_2H$, $CF_3CH_2CF_2CH_3$, $CF_3CF_2H$, $CH_3CF_2H$ (HFC-152a), $CF_3CH_2CH_2CF_3$ and $CHF_2CF_2CH_2F$, HCFCs such as $CH_3CCl_2F$, $CF_3CHCl_2$, and $CF_2HCl$, HCCs such as 2-chloropropane, and IFCs such as $CF_3I$, and HFEs such as $C_4F_9OCH_3$ and HFOs such as $CF_3CF=CH_2$, $CF_3CH=CHF$ and $CF_3CH=CHCl$. In certain formulations $CO_2$ generated from the reaction of water with foam precursor such as an isocyanate can be used as a blowing agent.

In various embodiments, the provided foamable composition may also include one or more foamable polymers or a precursor composition thereof. Foamable polymers suitable for use in the provided foamable compositions include, for example, polyolefins, e.g., polystyrene, poly(vinyl chloride), and polyethylene. Foams can be prepared from styrene polymers using conventional extrusion methods. The blowing agent composition can be injected into a heat-plastified styrene polymer stream within an extruder and admixed therewith prior to extrusion to form foam. Representative examples of suitable styrene polymers include, for example, the solid homopolymers of styrene, α-methylstyrene, ring-alkylated styrenes, and ring-halogenated styrenes, as well as copolymers of these monomers with minor amounts of other readily copolymerizable olefinic monomers, e.g., methyl methacrylate, acrylonitrile, maleic anhydride, citraconic anhydride, itaconic anhydride, acrylic acid, N-vinylcarbazole, butadiene, and divinylbenzene. Suitable vinyl chloride polymers include, for example, vinyl chloride homopolymer and copolymers of vinyl chloride with other vinyl monomers. Ethylene homopolymers and copolymers of ethylene with, e.g., 2-butene, acrylic acid, propylene, or butadiene may also be useful. Mixtures of different types of polymers can be employed. In various embodiments, the foamable compositions of the present disclosure may have a molar ratio of nucleating agent to blowing agent of no more than 1:50, 1:25, 1:9, or 1:7, 1:3, or 1:2.

Other conventional components of foam formulations can, optionally, be present in the foamable compositions of the present disclosure. For example, cross-linking or chain-extending agents, foam-stabilizing agents or surfactants, catalysts and fire-retardants can be utilized. Other possible components include fillers (e.g., carbon black), colorants, fungicides, bactericides, antioxidants, reinforcing agents, antistatic agents, and other additives or processing aids.

In some embodiments, polymeric foams can be prepared by vaporizing at least one liquid or gaseous blowing agent or generating at least one gaseous blowing agent in the presence of at least one foamable polymer or a precursor composition thereof and a nucleating agent as described above. In further embodiments, polymeric foams can be prepared using the provided foamable compositions by vaporizing (e.g., by utilizing the heat of precursor reaction) at least one blowing agent in the presence of a nucleating agent as described above, at least one organic polyisocyanate and at least one compound containing at least two reactive hydrogen atoms. In making a polyisocyanate-based foam, the polyisocyanate, reactive hydrogen-containing compound, and blowing agent composition can generally be combined, thoroughly mixed (using, e.g., any of the various known types of mixing head and spray apparatus), and permitted to expand and cure into a cellular polymer. It is often convenient, but not necessary, to preblend certain of the components of the foamable composition prior to reaction of the polyisocyanate and the reactive hydrogen-containing compound. For example, it is often useful to first blend the reactive hydrogen-containing compound, blowing agent composition, and any other components (e.g., surfactant) except the polyisocyanate, and to then combine the resulting mixture with the polyisocyanate. Alternatively, all components of the foamable composition can be introduced separately. It is also possible to pre-react all or a portion of the reactive hydrogen-containing compound with the polyisocyanate to form a prepolymer.

In some embodiments, the present disclosure is directed to dielectric fluids that include one or more hydrofluoroether compounds of the present disclosure, as well as to electrical devices (e.g., capacitors, switchgear, transformers, or electric cables or buses) that include such dielectric fluids. For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more hydrofluoroether compounds of the present disclosure and, optionally, one or more second dielectric fluids. Suitable second dielectric fluids include, for example, air, nitrogen, helium, argon, and carbon dioxide, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application are useful for electrical insulation and for arc quenching and current interruption equipment used in the transmission and distribution of electrical energy. Generally, there are three major types of electrical devices in which the fluids of the present disclosure can be used: (1) gas-insulated circuit breakers and current-interruption equipment, (2) gas-insulated transmission lines, and (3) gas-insulated transformers. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

In some embodiments, the present disclosure relates to coating compositions that include a solvent composition that one or more hydrofluoroether compounds of the present disclosure, and one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include perfluoropolyether, hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the hydrofluoroether compound function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more hydrofluoroether compounds of the present disclosure; and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the hydrofluoroether compound(s), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure relates to cleaning compositions that include one or more hydrofluoroether compounds of the present disclosure, and one or more co-solvents.

In some embodiments, the hydrofluoroether compounds may be present in an amount greater than 50 weight percent, greater than 60 weight percent, greater than 70 weight percent, or greater than 80 weight percent based upon the total weight of the hydrofluoroether compounds and the co-solvent(s)

In various embodiments, the cleaning composition may further comprise a surfactant. Suitable surfactants include those surfactants that are sufficiently soluble in the fluorinated olefin, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylatedalkyl phenols, ethoxylated fatty acids, alkylarysulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble oil removal. The surfactant, if used, can be added in an amount sufficient to promote soil removal. Typically, surfactant is added in amounts from about 0.1 to 5.0 wt. %, preferably in amounts from about 0.2 to 2.0 wt. % of the cleaning composition.

In illustrative embodiments, the co-solvent may include alcohols, ethers, alkanes, alkenes, haloalkenes, perfluorocarbons, perfluorinated tertiary amines, perfluoroethers, cycloalkanes, esters, ketones, aromatics, haloaromatics, siloxanes, hydrochlorocarbons, hydrochlorofluorocarbons, hydrofluorocarbons, or mixtures thereof. Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof.

In some embodiments, the present disclosure relates to a process for cleaning a substrate. The cleaning process can be carried out by contacting a contaminated substrate with a cleaning composition as discussed above. The hydrofluoroether compounds can be utilized alone or in admixture with each other or with other commonly-used cleaning solvents, e.g., alcohols, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrofluorocarbons, or mixtures thereof. Such co-solvents can be chosen to modify or enhance the solvency properties of a cleaning composition for a particular use and can be utilized in ratios (of co-solvent to hydrofluoroether compounds) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more hydrofluoroether compounds of the present disclosure and optionally one or more surfactants. Suitable surfactants include those surfactants that are sufficiently soluble in the hydrofluoroether compounds, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning processes of the disclosure can also be used to dissolve or remove most contaminants from the surface of a substrate. For example, materials such as light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; water; and other contaminants encountered in precision, electronic, metal, and medical device cleaning can be removed.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In some embodiments, the present disclosure further relates to electrolyte compositions that include one or more hydrofluoroether olefin compounds of the present disclosure. The electrolyte compositions may comprise (a) a solvent composition including one or more of the hydrofluoroether olefin compounds; and (b) at least one electrolyte salt. The electrolyte compositions of the present disclosure exhibit excellent oxidative stability, and when used in high voltage electrochemical cells (such as rechargeable lithium ion batteries) provide outstanding cycle life and calendar life. For example, when such electrolyte compositions are used in an electrochemical cell with a graphitized carbon electrode, the electrolytes provide stable cycling to a maximum charge voltage of at least 4.5V and up to 6.0V vs. Li/Li$^+$.

Electrolyte salts that are suitable for use in preparing the electrolyte compositions of the present disclosure include those salts that comprise at least one cation and at least one weakly coordinating anion (the conjugate acid of the anion having an acidity greater than or equal to that of a hydrocarbon sulfonic acid (for example, a bis(perfluoroalkanesulfonyl)imide anion); that are at least partially soluble in a selected hydrofluoroether compound (or in a blend thereof with one or more other hydrofluoroether compounds or one or more conventional electrolyte solvents); and that at least partially dissociate to form a conductive electrolyte composition. The salts may be stable over a range of operating voltages, are non-corrosive, and are thermally and hydrolytically stable. Suitable cations include alkali metal, alkaline earth metal, Group IIB metal, Group IIIB metal, transition metal, rare earth metal, and ammonium (for example, tetraalkylammonium or trialkylammonium) cations, as well as a proton. In some embodiments, cations for battery use include alkali metal and alkaline earth metal cations. Suitable anions include fluorine-containing inorganic anions such as $(FSO_2)_2N^-$, $BF_4^-$, $PF_6^-$, $AsF_6^-$, and $SbF_6^-$; $ClO_4^-$; $HSO_4^-$; $H_2PO_4^-$; organic anions such as alkane, aryl, and alkaryl sulfonates; fluorine-containing and nonfluorinated tetraarylborates; carboranes and halogen-, alkyl-, or haloalkylsubstituted carborane anions including metallocarborane anions; and fluorine-containing organic anions such as perfluoroalkanesulfonates, cyanoperfluoroalkanesulfonylamides, bis(cyano)perfluoroalkanesulfonylmethides, bis(perfluoroalkanesulfonyl)imides, bis(perfluoroalkanesulfonyl)methides, and tris(perfluoroalkanesulfonyl)methides; and the like. Preferred anions for battery use include fluorine-containing inorganic anions (for example, $(FSO_2)_2N^-$, $BF_4^-$, $PF_6^-$, and $AsF_6^-$) and fluorine-containing organic anions (for example, perfluoroalkanesulfonates, bis(perfluoroalkanesulfonyl)imides, and tris(perfluoroalkanesulfonyl)methides). The fluorine-containing organic anions can be either fully fluorinated, that is perfluorinated, or partially fluorinated (within the organic portion thereof). In some embodiments, the fluorine-containing organic anion is at least about 80 percent fluorinated (that is, at least about 80 percent of the carbon-bonded substituents of the anion are fluorine atoms). In some embodiments, the anion is perfluorinated (that is, fully fluorinated, where all of the carbon-bonded substituents are fluorine atoms). The anions, including the perfluorinated anions, can contain one or more catenary heteroatoms such as, for example, nitrogen, oxygen, or sulfur. In some embodiments, fluorine-containing organic anions include perfluoroalkanesulfonates, bis(perfluoroalkanesulfonyl)imides, and tris(perfluoroalkanesulfonyl)methides.

In some embodiments, the electrolyte salts may include lithium salts. Suitable lithium salts include, for example, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(fluorosulfonyl)imide (Li-FSI), and mixtures of two or more thereof.

The electrolyte compositions of the present disclosure can be prepared by combining at least one electrolyte salt and a solvent composition including at least one hydrofluoroether olefin compound of the present disclosure, such that the salt is at least partially dissolved in the solvent composition at the desired operating temperature. The hydrofluoroether compounds (or a normally liquid composition including, consisting, or consisting essentially thereof) can be used in such preparation.

In some embodiments, the electrolyte salt is employed in the electrolyte composition at a concentration such that the conductivity of the electrolyte composition is at or near its maximum value (typically, for example, at a Li molar concentration of around 0.1-4.0 M, or 1.0-2.0 M, for electrolytes for lithium batteries), although a wide range of other concentrations may also be employed.

In some embodiments, one or more conventional electrolyte solvents are mixed with the hydrofluoroether compound(s) (for example, such that the hydrofluoroether(s) constitute from about 1 to about 80 or 90 percent of the resulting solvent composition). Useful conventional electrolyte solvents include, for example, organic and fluorine-containing electrolyte solvents (for example, propylene carbonate, ethylene carbonate, dimethyl carbonate, diethyl carbonate, ethyl methyl carbonate, dimethoxyethane, 7-butyrolactone, diglyme (that is, diethylene glycol dimethyl ether), tetraglyme (that is, tetraethylene glycol dimethyl ether), monofluoroethylene carbonate, vinylene carbonate, ethyl acetate, methyl butyrate, tetrahydrofuran, alkyl-substituted tetrahydrofuran, 1, 3-dioxolane, alkyl-substituted 1, 3-dioxolane, tetrahydropyran, alkyl-substituted tetrahydropyran, and the like, and mixtures thereof). Other conventional electrolyte additives (for example, a surfactant) can also be present, if desired.

The present disclosure further relates to electrochemical cells (e.g., fuel cells, batteries, capacitors, electrochromic windows) that include the above-described electrolyte compositions. Such an electrochemical cells may include a positive electrode, a negative electrode, a separator, and the above-described electrolyte composition.

An electrochemical device using the electrolyte compositions described herein may, in some embodiments, have a discharge capacity of greater than 50%, preferably greater than 80% of theoretical, at a discharge current of up to 12 C. An electrochemical cell including the electrolyte composition described in this disclosure may, in some embodiments, have a charge capacity of greater than about 40%, preferably greater than about 60% of theoretical, at a charge current of up to 6 C. An electrochemical cell including the electrolyte compositions described herein may, in some embodiments, have excellent low temperature performance, and may retain over 90% of its discharge capacity at 25° C. when exposed to ambient temperatures from 0° C. to −20° C. The electrochemical cell including the presently described electrolyte compositions may, in some embodiments, retain a discharge capacity of greater than 150 mAh per gram of cathode over up to 30 charging cycles at up to 4.5V.

A variety of negative and positive electrodes may be employed in the electrochemical cells. Representative negative electrodes include graphitic carbons e. g., those having a spacing between (002) crystallographic planes, $d_{002}$, of 3.45 A>$d_{002}$>3.354 A and existing in forms such as powders, flakes, fibers or spheres (e. g., mesocarbon microbeads); $Li_{4/3}Ti_{5/3}O_4$ the lithium alloy compositions described in U. S. Pat. No. 6, 203, 944 (Turner '944) entitled "ELECTRODE FOR A LITHIUM BATTERY" and PCT Published Patent Application No. WO 00103444 (Turner PCT) entitled "ELECTRODE MATERIAL AND COMPOSITIONS"; and combinations thereof. Representative positive electrodes include $LiFePO_4$, $LiMnPO_4$, $LiCoPO_4$, $LiMn_2O_4$, $LiCoO_2$ and combinations thereof. The negative or positive electrode may contain additives such as will be familiar to those skilled in the art, e. g., carbon black for negative electrodes and carbon black, flake graphite and the like for positive electrodes.

The electrochemical devices of the invention can be used in various electronic articles such as computers, power tools, automobiles, telecommunication devices, and the like.

EMBODIMENTS

1. A hydrofluoroether compound represented by the following general formula (I):

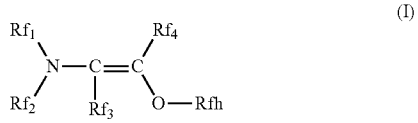

wherein,
(i) $Rf_3$ is F, $Rf_4$ is $CF_3$, and $Rf_1$ and $Rf_2$ are independently perfluoroalkyl groups (a) having 1 to 2 carbon atoms and optionally comprising at least one catenated heteroatom, or (b) that are bonded together to form a ring structure having 4-8 carbon atoms and optionally comprising one or more catenated heteroatoms selected from oxygen, nitrogen or sulfur; or
(ii) $Rf_3$ is $CF_3$, $Rf_4$ is F, and $Rf_1$ and $Rf_2$ are independently perfluoroalkyl groups (a) having 1 to 8 carbon atoms and optionally comprising at least one catenated heteroatom, or (b) that are bonded together to form a ring structure having 4 to 8 carbon atoms and optionally comprising one or more catenated heteroatoms selected from oxygen, nitrogen or sulfur; and wherein Rfh is a linear, branched, or cyclic alkyl or fluoroalkyl group of from 1 to 10 carbon atoms that may be saturated or unsaturated and optionally contains one or more catenated heteroatoms.

2. A hydrofluoroether compound represented by the following general formula (II):

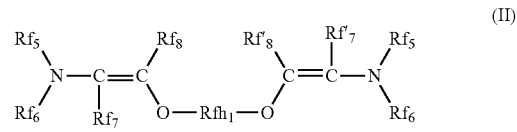

wherein,
$Rf_5$ and $Rf_6$ are independently perfluoroalkyl groups (i) having 1-8 carbon atoms and optionally comprising at least one catenated heteroatom, or (ii) that are bonded together to form a ring structure having 4-8 carbon atoms and optionally comprising one or more catenated heteroatoms selected from oxygen, nitrogen or sulfur. Each of $Rf_7$, $Rf_8$, $Rf'7$, and $Rf'_8$ is independently a F or $CF_3$ group, with the proviso that when:
$Rf_7$ is F, $Rf_8$ is $CF_3$,
$Rf_8$ is F, $Rf_7$ is $CF_3$,
$Rf'_7$ is F, $Rf'_8$ is $CF_3$,
$Rf'_8$ is F, $Rf'_7$ is $CF_3$, and
$Rfh_1$ is a linear, branched, cyclic, or acyclic alkylene or fluoroalkylene group having from 1 to 8 carbon atoms and optionally comprising one or more catenated heteroatoms.

3. A fire extinguishing composition comprising:
(a) a hydrofluoroether compound according to any one of embodiments 1-2;
(b) at least one co-extinguishing agent comprising one or more hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, and mixtures thereof, wherein (a) and (b) are present in an amount sufficient to suppress or extinguish a fire.

4. A fire extinguishing composition according to embodiment 3, wherein (a) and (b) are in a weight ratio of from about 9:1 to about 1:9.

5. A method of extinguishing a fire comprising:
applying to the fire a fire extinguishing composition comprising a hydrofluoroether compound according to any one of embodiments 1-2; and
suppressing the fire.

6. A method of extinguishing a fire according to embodiment 5, wherein the fire extinguishing composition further comprises at least one co-extinguishing agent comprising one or more hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, and mixtures thereof.

7. An apparatus for converting thermal energy into mechanical energy in a Rankine cycle comprising:
   a working fluid;
   a heat source to vaporize the working fluid and form a vaporized working fluid;
   a turbine through which the vaporized working fluid is passed thereby converting thermal energy into mechanical energy;
   a condenser to cool the vaporized working fluid after it is passed through the turbine; and
   a pump to recirculate the working fluid,
   wherein the working fluid comprises a hydrofluoroether compound according to any one of embodiments 1-2.

8. A process for converting thermal energy into mechanical energy in a Rankine cycle comprising:
   vaporizing a working fluid with a heat source to form a vaporized working fluid;
   expanding the vaporized working fluid through a turbine;
   cooling the vaporized working fluid using a cooling source to form a condensed working fluid; and
   pumping the condensed working fluid;
   wherein the working fluid comprises a hydrofluoroether compound according to any one of embodiments 1-2.

9. A process for recovering waste heat comprising:
   passing a liquid working fluid through a heat exchanger in communication with a process that produces waste heat to produce a vaporized working fluid;
   removing the vaporized working fluid from the heat exchanger;
   passing the vaporized working fluid through an expander, wherein the waste heat is converted into mechanical energy; and
   cooling the vaporized working fluid after it has been passed through the expander;
   wherein the working fluid comprises a hydrofluoroether compound according to any one of embodiments 1-2.

10. A foamable composition comprising:
    a blowing agent;
    a foamable polymer or a precursor composition thereof; and
    a nucleating agent, wherein said nucleating agent comprises a hydrofluoroether compound according to any one of embodiments 1-2.

11. A foamable composition according to embodiment 10, wherein the nucleating agent and the blowing agent are in a molar ratio of less than 1:2.

12. A foamable composition according to any one of embodiments 10-11, wherein the blowing agent comprises an aliphatic hydrocarbon having from about 5 to about 7 carbon atoms, a cycloaliphatic hydrocarbon having from about 5 to about 7 carbon atoms, a hydrocarbon ester, water, or combinations thereof.

13. A process for preparing polymeric foam comprising:
    vaporizing at least one liquid or gaseous blowing agent or generating at least one gaseous blowing agent in the presence of at least one foamable polymer or a precursor composition thereof and a nucleating agent, wherein said nucleating agent comprises a hydrofluoroether compounding according to any one of embodiments 1-2.

14. A foam made with the foamable composition according to embodiment 12.

15. A device comprising:
    a dielectric fluid comprising a hydrofluoroether compound according to any one of embodiments 1-2;
    wherein the device is an electrical device.

16. The device of embodiment 15, wherein said electrical device comprises a gas-insulated circuit breakers, current-interruption equipment, a gas-insulated transmission line, a gas-insulated transformers, or a gas-insulated substation.

17. The device according to any one of embodiments 15-16, wherein the dielectric fluid further comprises a second dielectric gas.

18. The device of embodiment 17, wherein the second dielectric gas comprises an inert gas.

19. The device of embodiment 18, wherein the second dielectric gas comprises nitrogen, helium, argon, or carbon dioxide.

20. A coating composition comprising:
    a solvent composition comprising a hydrofluoroether compound according to any one of embodiments 1-2; and
    a coating material that is soluble or dispersible in said solvent composition.

21. The coating composition according to embodiment 20, wherein said coating material comprises a pigment, lubricant, stabilizer, adhesive, anti-oxidant, dye, polymer, pharmaceutical, release agent, inorganic oxide.

22. The composition according to embodiment 20, wherein said coating material comprises a perfluoropolyether, a hydrocarbon, a silicone lubricant, a copolymer of tetrafluoroethylene, or a polytetrafluoroethylene.

23. A cleaning composition comprising:
    a hydrofluoroether compound according to any one of embodiments 1-2; and
    a co-solvent.

24. The composition of embodiment 24, wherein said hydrofluoroether compound is greater than 50 percent by weight of said composition based on the total weights of the fluorinated olefin compound and the co-solvent.

25. The composition according to any one of embodiments 23-24, wherein said co-solvent comprises alcohols, ethers, alkanes, alkenes, haloalkenes, perfluorocarbons, perfluorinated tertiary amines, perfluoroethers, cycloalkanes, esters, ketones, aromatics, haloaromatics, siloxanes, hydrochlorocarbons, hydrochlorofluorocarbons, hydrofluorocarbons, or mixtures thereof.

26. A cleaning composition comprising:
    a hydrofluoroether compound according to any one of embodiments 1-2; and
    a surfactant.

27. The composition of embodiment 26, wherein the cleaning composition comprises from 0.1 to 5 percent by weight surfactant.

28. The composition according to any one of embodiments 26-27, wherein the surfactant comprises a nonionic surfactant comprising an ethoxylated alcohol, an ethoxylated alkylphenol, an ethoxylated fatty acid, an alkylaryl sulfonate, a glycerolester, an ethoxylated fluoroalcohol, a fluorinated sulfonamide, or mixtures thereof.

29. A process for removing contaminants from a substrate, the process comprising the steps of:
    contacting a substrate with a composition comprising:
       a hydrofluoroether compound according to any one of embodiments 1-2; and
       a co-solvent.

30. An electrolyte composition comprising:
    a solvent composition comprising at least one hydrofluoroether compound according to any one of embodiments 1-2; and
    an electrolyte salt.

The operation of the present disclosure will be further described with regard to the following detailed examples. These examples are offered to further illustrate various embodiments and techniques. It should be understood, however, that many variations and modifications may be made while remaining within the scope of the present disclosure.

EXAMPLES

Example 1

Preparation of 2,2,3,3,5,5,6,6-octafluoro-4-(1,3,3,3-tetrafluoro-2-methoxy-prop-1-enyl)morpholine

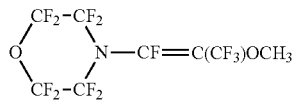

2,2,3,3,5,5,6,6-octafluoro-4-(1,2,3,3,3-pentafluoroprop-1-enyl)morpholine was prepared using a hot tube reactor. To the hot tube reactor (metallurgy), anhydrous potassium carbonate (400 g, 2.9 mol, Sigma-Aldrich) was charged. The reactor was sealed and connected to a high pressure syringe pump. The reactor was heated to a temperature of 220° C. 2-[difluoro-(2,2,3,3,5,5,6,6-octafluoromorpholin-4-yl)methyl]-2,3,3,3-tetrafluoro-propanoyl fluoride (470 g 1.1 mol) (prepared via electrochemical fluorination of methyl 2-methyl-3-morpholino-propanoate via a Simons ECF cell of essentially the type described in U.S. Pat. No. 2,713,593 (Brice et al.) and in R. E. Banks, Preparation, Properties and Industrial Applications of Organofluorine Compounds, pages 19-43, Halsted Press, New York (1982)) was then pumped to the hot tube reactor at a rate of 35 mL/hour. The product was collected using a dry ice trap at −78° C. A total of 345 g of material was collected which was ~70% converted to the desired product. The remaining material was unreacted acid fluoride and inert fluorocarbon. The material was fractionally distilled and its boiling point is about 85° C. The product structure was verified by GC/MS and F-19 and H-1 NMR.

In a 500 mL round bottom flask equipped with magnetic stirring, condenser controlled with a chiller at 1 deg. C., addition funnel and dry N2 bubbler, 2,2,3,3,5,5,6,6-octafluoro-4-(1,2,3,3,3-pentafluoroprop-1-enyl)morpholine (220 g, 0.61 mol), potassium hydroxide (39.9 g, 0.713 mol, Sigma-Aldrich) and Aliquat 336 (1 g, 0.002 mol, Alfa-Aesar) were charged. The mix was stirred at room temp and methanol (19.5 g, 0.61 mol, Alfa-Aesar) was added slowly dropwise via an addition funnel over an hour. Once the methanol charge was added the reaction mixture was heated to 65° C. for 16 hours. After stirring overnight the heat was removed and after cooling to room temperature, 100 mL of water was added. The mix was stirred and then transferred to a 500 mL separatory funnel. The lower FC phase was separated and dried with anhydrous magnesium sulfate. A total of 138 g of material was collected. Based on GC-FID analysis, the conversion to the desired product was about 75%. This material was fractionally distilled using a concentric tube column. The boiling point of the product is approximately 128° C. The product structure was confirmed to be a mixture of cis and trans isomers by GC/MS and F-19 and H-1 NMR.

Example 2

Preparation of 2,2,3,3,5,5,6,6-octafluoro-4-[2-fluoro-2-methoxy-1-(trifluoromethyl)vinyl]morpholine

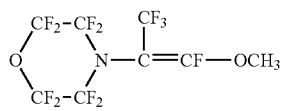

4-[2,2-difluoro-1-(trifluoromethyl)vinyl]-2,2,3,3,5,5,6,6-octafluoro-morpholine was prepared by converting 2,2,3,4,4,4-hexafluoro-3-(2,2,3,3,5,5,6,6-octafluoromorpholin-4-yl)butanoyl fluoride (prepared via electrochemical fluorination of methyl 3-morpholinobutanoate via a Simons ECF cell of essentially the type described in U.S. Pat. No. 2,713,593 (Brice et al.) and in R. E. Banks, Preparation, Properties and Industrial Applications of Organofluorine Compounds, pages 19-43, Halsted Press, New York (1982)) to the potassium salt via titration of methyl 2,2,3,4,4,4-hexafluoro-3-(2,2,3,3,5,5,6,6-octafluoromorpholin-4-yl)butanoate with potassium hydroxide. Potassium 2,2,3,4,4,4-hexafluoro-3-(2,2,3,3,5,5,6,6-octafluoromorpholin-4-yl)butanoate (134 g, 0.29 mol) and 200 mL of HT-270 (Solvay-Solexis) were charged to a 500 mL 3-neck round bottom flask. The flask was equipped with overhead stirring, thermocouple, heating mantle and a one-plate simple distillation column. The mixture was gradually heated up to 210° C. A total of 86 g of 4-[2,2-difluoro-1-(trifluoromethyl)vinyl]-2,2,3,3,5,5,6,6-octafluoro-morpholine was collected of which about 70% was the desired product with the remainder being inert fluorocarbon. The reaction was repeated on another portion of potassium salt and in total 196 g of the desired olefin intermediate were obtained.

In a 3-neck 250 mL round bottom flask powdered potassium hydroxide (14.16 g, 0.253 mol Sigma-Aldrich), 4-[2,2-difluoro-1-(trifluoromethyl)vinyl]-2,2,3,3,5,5,6,6-octafluoro-morpholine (110 g 0.216 mol) and Aliquat 336 (1 g, 0.0024 mol) were charged. The flask was equipped with overhead stirring, a cold water condenser, thermocouple and heating mantle. Methanol (6.93 g, 0.216 mol Sigma-Aldrich) was added via an addition funnel and the reaction mixture was kept cool during the addition with a cold water bath. Once the methanol addition was complete, the reaction was heated to 65 deg. C. for 24 hours. Water was then added to the mix to dissolve the salts. The mixture was then transferred to a separatory funnel where the fluorochemical phase was separated from the aqueous phase. 89 g of crude product was collected after phase splitting. The fluorochemical was dried over anhydrous $MgSO_4$ and then fractionally distilled using a concentric tube distillation column. A sample of the main distillate cut (B.P.=125° C.) was analyzed by GC/MS, confirming the presence of the desired product.

Example 3

Preparation of 2,2,3,3,5,5,6,6-octafluoro-4-[1,3,3,3-tetrafluoro-2-(2,2,3,3-tetrafluoropropoxy)prop-1-enyl]morpholine

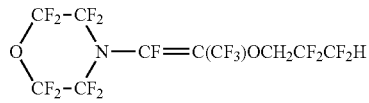

2,2,3,3,5,5,6,6-octafluoro-4-[(E&Z)-1,2,3,3,3-pentafluoroprop-1-enyl]morpholine (200.00 g, >95%), acetonitrile (312 g, Aldrich Anhydrous, 99.8%) and potassium carbonate (84.214 g, powdered, 325 mesh, Armand Product Co.) were combined in a 3-neck 1000 mL round bottom flask equipped with magnetic stirring, a water cooled condenser with N2 inlet, a Claisen adapter with Teflon coated thermocouple probe and addition funnel, While reaction mixture was stirring 2,2,3,3-tetrafluoropropanol (76.809 g, TCI America, >98%) was charged to the reaction mixture over 90 minutes. A slightly exothermic reaction was observed causing the reaction temperature to rise from 21.3° to 24.4° C. The reaction was allowed to proceed for 18 hours at which time stirring was halted and a sample of the bottom layer was removed by pipette and filtered through a 0.2 μm PVDF filter disc. This filtered sample was analyzed by GC-FID showing the starting propenylamine is 69.8% converted. An additional 20.83 g potassium carbonate was charged to the reaction mixture in several portions with stirring at room temperature resulting in a final overall measured conversion (by GC) of 95%. The product mixture contained 79% of the desired Hydrofluoroether-Olefin (HFE-Olefin) product and 5% of the corresponding HFE-Hydride, O(CF$_2$CF$_2$)$_2$NCF-HCF(CF$_3$)OCH$_2$CF$_2$CF$_2$H. The crude reaction mix was filtered through a C porosity fritted glass filter funnel to remove solids. The filtrate was fractionally distilled to remove a majority of the residual starting propenylamine, CH$_3$CN and unreacted HOCH$_2$CF$_2$CF$_2$H. The fractional distillation was allowed to proceed until the head temp reached 156° C. The crude product remaining in the distillation pot was straw colored and contained some insoluble dark sludgy solids. This mixture was filtered through a 1 μm glass filter disc to remove solids, giving a colored filtrate. The filtered crude product was transferred to a 250 mL poly bottle, diluted with 142 g acetonitrile and treated with 6.36 g KOH powder in two portions to convert all residual HFE-Hydride byproduct to the desired HFE-Olefin product (by dehydrofluorination). After stirring with KOH at room temperature for at least a few hours, the treated mixture was filtered by suction through a C porosity fritted glass filter. The desired product was then isolated from the filtrate and purified by fractional distillation through a concentric tube distillation column giving 45.63 g of product distillate (B.P.=161-162° C.) as a clear colorless liquid with an average purity of 97.84% by GC. The product structure, consisting of a mixture of E and Z isomers, was verified by GC/MS and $^{19}$F and $^1$H NMR spectroscopy.

Example 4

Preparation of 1,3,3,3-tetrafluoro-2-methoxy-N-(1,1,2,2,2-pentafluoroethyl)-N-(trifluoromethyl)prop-1-en-1-amine

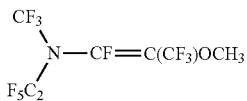

Potassium carbonate (325 mesh) (0.456 g, 3.30 mmol), 1,2,3,3,3-pentafluoro-N-(1,1,2,2,2-pentafluoroethyl)-N-(trifluoromethyl)prop-1-en-1-amine (1 g, 3.00 mmol), and acetonitrile (anhydrous) (2.358 g, 3 mL) were added to an 8 mL screw cap vial equipped with a Teflon coated magnetic stir bar. Methanol was then added and the biphasic reaction mixture is allowed to stir at room temperature for 96 h. The propenylamine starting material was 44% converted (by GC) under these conditions. The reaction mixture was filtered through a 0.2 μm PVDF filter disc and then diluted with water to cause the fluorochemical product mixture to phase separate and to remove residual base and acetonitrile in the upper water phase. The lower fluorochemical phase was analyzed by GC-MS, which verified that the desired HFE-Olefin product, consisting of a mixture of E and Z isomers, was present at 91.3% of the overall mixture. No HFE-Hydride byproduct was detected.

The following examples (5-11) use the general procedure (A) outlined here: Potassium hydroxide (fine powder), alcohol, and acetonitrile are added to an 8 mL screw cap vial equipped with a Teflon coated magnetic stir bar. (E/Z)-2,2,3,3,5,5,6,6-octafluoro-4-(perfluoroprop-1-en-1-yl)morpholine is then added and the biphasic reaction mixture is allowed to stir at r.t. for 16 h. The resulting mixture is then diluted with water and the fluorochemical phase is analyzed using GC, GC/MS and NMR.

Example 5

Preparation of E/Z—N,N-dimethyl-2-((1,3,3,3-tetrafluoro-1-(perfluoromorpholino)prop-1-en-2-yl)oxy)ethan-1-amine Following General Procedure A, (E/Z)-2,2,3,3,5,5,6,6-octafluoro-4-(perfluoroprop-1-en-1-yl)morpholine (1 equiv., 4.71 mmol, 1 mL), KOH (1.2 equiv, 5.65 mmol, 316.99 mg), 2-(dimethylamino)ethan-1-ol (1.2 equiv., 5.65 mmol, 518.56 μL) and acetonitrile (1 mL) were added. Analysis by GC and GC/MS indicates 88% yield of the desired product as a mixture of E/Z isomers

Example 6

Preparation of (E/Z)-2,2,3,3,5,5,6,6-octafluoro-4-(1,3,3,3-tetrafluoro-2-(2-methoxyethoxy)prop-1-en-1-yl)morpholine

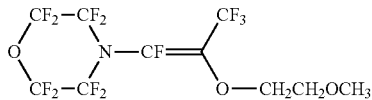

Following General Procedure A, (E/Z)-2,2,3,3,5,5,6,6-octafluoro-4-(perfluoroprop-1-en-1-yl)morpholine (1 equiv., 4.71 mmol, 1 mL), KOH (1.2 equiv, 5.65 mmol, 316.99 mg), 2-methoxyethan-1-ol (1.2 equiv., 5.65 mmol, 445.53 μL) and acetonitrile (1 mL) were added. Analysis by GC and GC/MS indicates 78% yield of the desired product as a mixture of E/Z isomers.

Example 7

Preparation of (E/Z)-4-(2-(cyclopentyloxy)-1,3,3,3-tetrafluoroprop-1-en-1-yl)-2,2,3,3,5,5,6,6-octafluoro-morpholine

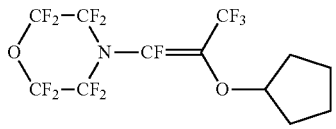

Following General Procedure A, (E/Z)-2,2,3,3,5,5,6,6-octafluoro-4-(perfluoroprop-1-en-1-yl)morpholine (1 equiv., 4.71 mmol, 1 mL), KOH (1.2 equiv, 5.65 mmol, 316.99 mg), cyclopentanol (1.2 equiv., 5.65 mmol, 512.81 μL) and acetonitrile (1 mL) were added. Analysis by GC and GC/MS indicates 51% yield of the desired product as a mixture of E/Z isomers.

Example 8

Preparation of (E/Z)-4-(2-(cyclopropylmethoxy)-1,3,3,3-tetrafluoroprop-1-en-1-yl)-2,2,3,3,5,5,6,6-octafluoromorpholine

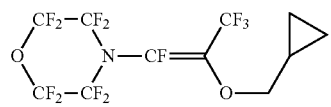

Following General Procedure A, (E/Z)-2,2,3,3,5,5,6,6-octafluoro-4-(perfluoroprop-1-en-1-yl)morpholine (1 equiv., 4.71 mmol, 1 mL), KOH (1.2 equiv, 5.65 mmol, 316.99 mg), cyclopropylmethanol (1.2 equiv., 5.65 mmol, 457.76 μL) and acetonitrile (1 mL) were added. Analysis by GC and GC/MS indicates 88% yield of the desired product as a mixture of E/Z isomers.

Example 9

Preparation of 2,2,3,3,5,5,6,6-octafluoro-4-((E/Z)-1,3,3,3-tetrafluoro-2-(((E)-4,4,4-trifluorobut-2-en-1-yl)oxy)prop-1-en-1-yl)morpholine

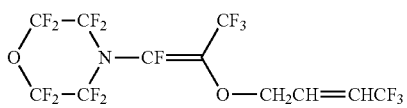

Following General Procedure A, (E/Z)-2,2,3,3,5,5,6,6-octafluoro-4-(perfluoroprop-1-en-1-yl)morpholine (1 equiv., 4.71 mmol, 1 mL), KOH (1.2 equiv, 5.65 mmol, 316.99 mg), (E)-4,4,4-trifluorobut-2-en-1-ol (1.2 equiv., 5.65 mmol, 567.15 μL) and acetonitrile (1 mL) were added. Analysis by GC and GC/MS indicates 76% yield of the desired product as a mixture of E/Z isomers.

Example 10

Preparation of (E/Z)-2,2,3,3,5,5,6,6-octafluoro-4-(1,3,3,3-tetrafluoro-2-((3-methylbut-2-en-1-yl)oxy)prop-1-en-1-yl)morpholine

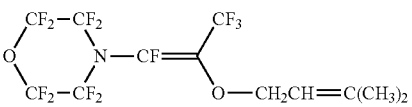

Following General Procedure A, (E)-2,2,3,3,5,5,6,6-octafluoro-4-(perfluoroprop-1-en-1-yl)morpholine (1 equiv., 4.71 mmol, 1 mL), KOH (1.2 equiv, 5.65 mmol, 316.99 mg), 3-methylbut-2-en-1-ol (1.2 equiv., 5.65 mmol, 565.88 μL) and acetonitrile (1 mL) were added. Analysis by GC and GC/MS indicates 85% yield of the desired product as a mixture of E/Z isomers.

Example 11

Preparation of 1-(((E/Z)-1,3,3,3-tetrafluoro-1-(perfluoromorpholino)prop-1-en-2-yl)oxy)-4-(((E/Z)-1,3,3,3-tetrafluoro-1-(perfluoromorpholino)prop-1-en-2-yl)oxy)butane

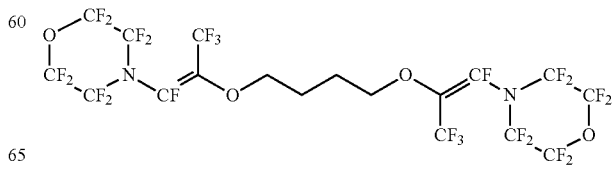

Following General Procedure A, (E/Z)-2,2,3,3,5,5,6,6-octafluoro-4-(perfluoroprop-1-en-1-yl)morpholine (1 equiv., 4.71 mmol, 1 mL), KOH (1.2 equiv, 5.65 mmol, 316.99 mg), 1,4-butandiol (0.5 equiv., 2.35 mmol, 208.62 μL) and acetonitrile (1 mL) were added. Analysis by GC and GC/MS indicates 56% yield of the desired product as a mixture of E/Z isomers.

Examples 12-19

The following examples were prepared by the following general method: K$_2$CO$_3$ powder, anhydrous CH$_3$CN, PF-propenylamine and the alcohol reagent were charged to a 7 mL glass vial in the order indicated (in air). A mini stir bar was added and the vial was then tightly capped and rapid stirring initiated at the temperature indicated in the Table. The reaction was allowed to proceed with stirring for a minimum of 16 hours, while monitoring the progress of the reaction periodically by GC-FID by removing small aliquots of the reaction mixture and injecting neat. Once the reaction was judged to be nearly complete, the reaction solution was filtered by syringe to remove suspended solids and the filtrate was submitted for GC-MS analysis to confirm tentative GC-FID peak assignments and identify the major products formed. This information was then used to calculate the yield of the desired alcohol addition products and the olefin/hydride ratio.

| Ex | PF-Propenylamine | mMoles | Alcohol | mMoles | K2CO3 (mMoles) | CH3CN Solvent (mLs) | Rxn Time (Hrs) | Reaction Temp °C. | GC Area % Yield of Desired * | Olefin/ Hydride Ratio ** |
|----|------------------|--------|---------|--------|----------------|---------------------|----------------|-------------------|------------------------------|--------------------------|
| 12 | morpholine-CF=CFCF3 | 2.770 | CF3CH2OH | 2.909 | 4.494 | 3 | 96 | 21 | 89.6 | 11.1 |
| 13 | morpholine-CF=CFCF3 | 2.770 | HCF2CF2CH2OH | 2.909 | 3.843 | 3 | 48 | 21 | 84.3 | 17.3 |
| 14 | morpholine-CF=CFCF3 | 2.770 | CF3CFHCF2CH2OH | 2.909 | 2.909 | 3 | 96 | 22 | 87.2 | 22.7 |
| 15 | morpholine-CF=CFCF3 | 2.770 | C2F5CH2OH | 2.909 | 2.909 | 3 | 96 | 22 | 79.9 | 34.6 |
| 16 | morpholine-CF=CFCF3 | 2.770 | (CF3)2CHOH | 2.909 | 2.909 | 3 | 72 | 22 | 75.1 | 3.9 |
| 17 | morpholine-CF=CFCF3 | 2.770 | CF3CFHCF2CH(CH3)OH | 2.909 | 2.909 | 3 | 96 | 22 | 90.0 | 59.5 |
| 18 | (C2F5)(CF3)N-CF=CFCF3 | 3.003 | HCF2CF2CH2OH | 3.299 | 3.299 | 3 | 96 | 22 | 95.9 | 66.7 |
| 19 | (C2F5)(CF3)N-CF=CFCF3 | 3.003 | CF3CFHCF2CH2OH | 3.299 | 3.299 | 3 | 96 | 22 | 91.2 | 33.3 |

\* Based on conversion of PF-Propenylamine (limiting reagent) to desired HFE-Olefin (major) and HFE-Hydride (minor byproduct) addition products by GC-FID. Byproduct HFE-Hydride is readily converted back to desired HFE-Olefin by treatment with strong base (e.g., KOH, etc).
\*\* HFE-Olefin/HFE-Hydride ratio by relative GC-FID peak area Using the procedure and reagents described in Examples 12-19, the following hydrofluoroether (or HFE-Olefin) compounds (a mixture of E and Z isomers) were successfully prepared in high yield and characterized by GC-MS:

| Ex | Product |
|----|---------|
| 12 | morpholine-N-CF=C(CF3)(OCH2CF3) |
| 13 | morpholine-N-CF=C(CF3)(OCH2CF2CF2H) |
| 14 | morpholine-N-CF=C(CF3)(OCH2CF2CFHCF3) |

| Ex | Product |
|---|---|
| 15 | 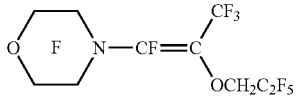 |
| 16 | 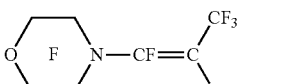 |
| 17 | 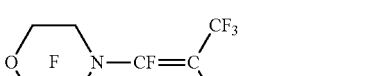 |
| 18 | 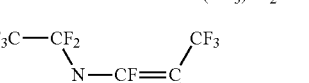 |
| 19 | 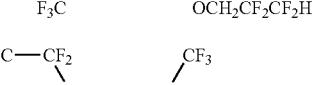 |

Example 20

Preparation of 1,3,3,3-tetrafluoro-2-(2,2,3,3-tetrafluoropropoxy)-N,N-bis(trifluoromethyl)prop-1-en-1-amine

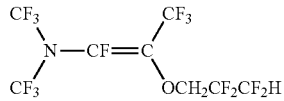

(E&Z)-1,2,3,3,3-pentafluoro-N,N-bis(trifluoromethyl) prop-1-ene-1-amine (200.00 g, 99.9%), acetone (395.5 g, EMD HPLC Grade) and potassium carbonate (107.42 g, powdered, 325mesh, Armand Product Co.) were combined in a 3-neck, 1000 mL round bottom flask equipped with magnetic stirring, a chiller cooled condenser set to 0° C. with N2 inlet, a Claisen adapter with Teflon coated thermocouple probe and addition funnel. The starting reaction mixture initially contained two liquid phases. While reaction mixture was stirring at room temperature, 2,2,3,3-tetrafluoropropanol (97.98 g, TCI America, >98%) was added over a 90 minute period. A slightly exothermic reaction was observed causing the reaction temperature to rise from 21.3° to 24.4° C. The reaction mixture appeared to be a single liquid phase once alcohol addition was complete. The reaction was allowed to proceed at room temperature for 48 hours after which time stirring was halted and a sample of the reaction was removed by pipette and filtered through a 0.2 μm PVDF filter disc. This filtered sample was analyzed by GC-FID showing the starting propenyl amine was 82% converted. An additional 19.88 g potassium carbonate was charged to the mixture and the reaction was allowed to proceed for an additional 3 days at room temperature with stirring. Analysis by GC-FID, as described above, indicated that the reaction was 91% complete (i.e., 9% of the starting material remained). An additional 20.14 g potassium carbonate was charged to the reaction mixture and allowed to stir for another 24 hours. Then stirring was halted and the bottom layer of the reaction mixture was evaluated by GC-FID. The amount of propenyl amine starting material converted was >95%. The crude reaction mixture was filtered through 20-25 μm filter paper to remove solids. The filtrate collected was transferred to a separatory funnel and washed with 500 mL water causing the dense fluorochemical product phase to separate from the upper aqueous phase. The fluorochemical phase was isolated and washed twice with additional water. GC analysis indicated that the crude fluorochemical product was 99.70% desired product mixture, consisting of 96.59% desired HFE-Olefin and 3.11% HFE-Hydride byproduct. The residual HFE-Hydride byproduct was converted to the desired HFE-Olefin product (by dehydrofluorination) by treatment of the crude product at room temperature with 8.69 g potassium hydroxide (powdered, Fluka, >85%) charged in three portions along with 3.25 g acetonitrile (Aldrich Anhydrous, 99.8). Three 100 mL water washes were used to remove residual potassium hydroxide and acetonitrile from the treated product. The fluorochemical product phase was then dried over 3A molecular sieves for 5 days, and purified by fractional distillation through a concentric tube distillation column giving 110.64 g of product distillate (B.P.=120-124° C.) as a clear colorless liquid with an average purity of 99.63% by GC. The product structure, consisting of a mixture of E and Z isomers, was verified by GC/MS and $^{19}F$ and $^{1}H$ NMR spectroscopy.

Example 21

Preparation of 4-[2-ethoxy-1,3,3,3-tetrafluoro-prop-1-enyl]-2,2,3,3,5,5,6,6-octafluoro-morpholine

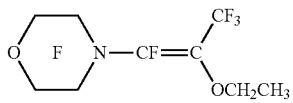

2,2,3,3,5,5,6,6-octafluoro-4-[(E&Z)-1,2,3,3,3-pentafluoroprop-1-enyl]morpholine (200.00 g, >95%), acetonitrile (312 g, Aldrich Anhydrous, 99.8%) and potassium hydroxide (32.63 g, powdered, Fluka, >85%) were combined in a 3-neck 1000 mL round bottom flask equipped with magnetic stirring, a water cooled condenser with N2 inlet, a Claisen adapter with Teflon coated thermocouple probe and addition funnel, While reaction mixture was stirring at room temperature, ethanol (26.80 g, undenatured, 200 proof) was charged to the reaction mixture over a 75 minute period. A slightly exothermic reaction was observed causing the reaction temperature to rise from 22.2° to 24.6°. The reaction was allowed to proceed for 24 hours after which time stirring was halted and a sample of the bottom layer was removed by pipette and filtered through a 0.2 μm PVDF filter disc. This filtered sample was analyzed by GC-FID indicating that the starting propenyl amine was 82% converted. An additional 9.46 g potassium hydroxide was charged to the reaction mixture in several portions with stirring at room temperature. The reaction was allowed to proceed overnight at room temperature. Then, stirring was halted and the bottom layer of the reaction mixture was evaluated as above by GC-FID, indicating that >98% of the starting material was converted. The fluorochemical product mixture contained 96% desired product (HFE-Olefin) and 1% HFE-Hydride byproduct, $O(CF_2CF_2)_2NCFHCF(CF_3)OCH_2CH_3$, by GC. The crude reaction mix was filtered through 20-25 μm filter paper to remove insoluble solids. The filtrate was combined with 100 mL of water causing the dense fluorochemical product to phase separate from the upper aqueous layer. The crude fluorochemical product phase was isolated, dried over 3A molecular sieves, and purified by fractional distillation using a concentric tube distillation column. Fractional distillation proved incapable of removing all the residual $CH_3CN$ solvent and HFE-Hydride byproduct, so the collected product distillate fractions were recombined, treated with 2 portions of KOH(powder) (4.80 g total) and stirred overnight at room temperature to convert all residual HFE-Hydride byproduct to the desired HFE-Olefin product (by dehydrofluorination). The treated product mixture was then filtered through 20-25 μm filter paper to remove the insoluble KOH solids and washed with three 50 mL portions of DI water to remove the residual acetonitrile. The washed fluorochemical phase was transferred to an Erlenmeyer flask, dried over 3A molecular sieves for three days, and then purified by fractional distillation through a concentric tube distillation column. A total of 71.69 g of product distillate was collected as a clear colorless liquid (B.P.=136-141° C.) with an average purity of 99.64% by GC. The product structure, consisting of a mixture of E and Z isomers, was verified by GC/MS and $^{19}F$ and $^1H$ NMR spectroscopy.

Example 22

Preparation of 2,3,3,5,5,6-hexafluoro-4-(1,3,3,3-tetrafluoro-2-methoxy-prop-1-enyl)-2,6-bis(trifluoromethyl)morpholine

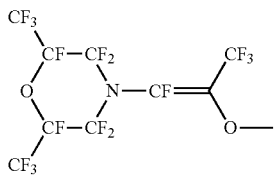

In a 100 mL 2-neck round bottom flask equipped with magnetic stirring, cold water condenser, dry N2 bubbler and a thermocouple, 2,3,3,5,5,6-hexafluoro-4-(1,2,3,3,3-pentafluoroprop-1-enyl)-2,6-bis(trifluoromethyl)morpholine (13 g, 28.2 mmol), powdered potassium hydroxide (1.9 g, 29 mmol), acetonitrile (50 mL), methanol (1.1 g, 34 mmol) and Adogen 464 (0.42 g, 1.0 mmol) were combined and stirred for 16 hours at 50 deg. C. A sample of the fluorochemical phase was then analyzed by GC-FID and GC/MS which showed 49.2% of the desired product structure.

The following examples (23-24) use the general procedure (B) outlined here: Potassium hydroxide (fine powder), alcohol, and acetonitrile were added to an 7 mL screw cap vial equipped with a Teflon coated magnetic stir bar. (E/Z)-1,2,3,3,3-pentafluoro-N-(1,1,2,2,2-pentafluoroethyl)-N-(trifluoromethyl)prop-1-en-1-amine was then added and the biphasic reaction mixture was allowed to stir at r.t. for 17 h. The resulting mixture was then filtered via syringe through a 0.45 micron Teflon membrane to remove solids and analyzed by GC-FID and GC/MS.

Example 23

Preparation of (E/Z)-2-ethoxy-1,3,3,3-tetrafluoro-N-(1,1,2,2,2-pentafluoroethyl)-N-(trifluoromethyl)prop-1-en-1-amine

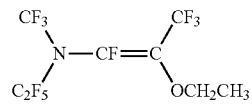

Following General Procedure B, (E/Z)-1,2,3,3,3-pentafluoro-N-(1,1,2,2,2-pentafluoroethyl)-N-(trifluoromethyl)prop-1-en-1-amine (1 equiv., 3.00 mmol, 1.0 g), KOH (1.6 equiv, 4.80 mmol, 270 mg), and ethanol (1.2 equiv., 3.60 mmol, 210 μL) were reacted in acetonitrile (3 mL). Analysis of the acetonitrile solution by GC and GC/MS indicates 94.4% yield of the desired HFE-Olefin product was obtained as a mixture of E/Z isomers, based on limiting reagent.

Example 24

Preparation of (E/Z)-1,3,3,3-tetrafluoro-N-(1,1,2,2,2-pentafluoroethyl)-2-[2,2,3,3-tetrafluoro-4-[(E/Z)-2-fluoro-2-[1,1,2,2,2-pentafluoroethyl(trifluoromethyl)amino]-1-(trifluoromethyl)vinyloxy]butoxy]-N-(trifluoromethyl)prop-1-en-1-amine

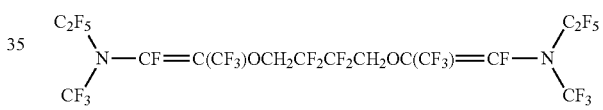

Following General Procedure B, (E/Z)-1,2,3,3,3-pentafluoro-N-(1,1,2,2,2-pentafluoroethyl)-N-(trifluoromethyl)prop-1-en-1-amine (3 equiv., 6.01 mmol, 2.0 g), KOH (2.2 equiv, 4.40 mmol, 247 mg), 2,2,3,3-tetrafluorobutane-1,4-diol (1.0 equiv., 2.00 mmol, 0.324 g) were reacted in acetonitrile (4 mL). A small amount of Aliquat 336 (N-Methyl-N,N-dioctan-1-ammonium chloride, 0.15 mmol, 0.12 g) was also charged to the reaction mixture as a phase transfer catalyst to facilitate the biphasic reaction. Analysis of the lower insoluble fluorochemical phase by GC and GC/MS indicates that 100% of the starting diol reagent was consumed. The yield of the desired difunctional HFE-Olefin was 77.95% as a mixture of E/Z isomers, based on limiting reagent.

Example 25

Preparation of 1,3,3,3-tetrafluoro-2-methoxy-N,N-bis(trifluoromethyl)prop-1-en-1-amine

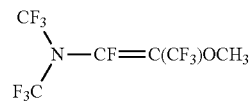

1,2,3,3,3-pentafluoro-N,N-bis(trifluoromethyl)prop-1-en-1-amine was prepared by reaction of 2-[[bis(trifluoromethyl)amino]-difluoro-methyl]-2,3,3,3-tetrafluoro-propanoyl fluoride with anhydrous potassium carbonate in a 2 liter stainless steel non-stirred reactor equipped with inlet and outlet ports. Vacuum oven dried potassium carbonate (2500 grams, 18.09 moles) was charged to the reactor and the reactor was heated to 220 C. 2-[[bis(trifluoromethyl)amino]-difluoro-methyl]-2,3,3,3-tetrafluoro-propanoyl fluoride (1274.5 grams, 83.0% purity, 3.0 moles) made by Simons electrochemical fluorination of methyl 3-(dimethylamino)-2-methyl-propanoate was added through a dip tube at a rate of 100 ml/hour. The gas from the reactor was collected in a dry ice cooled receiver. 1,2,3,3,3-pentafluoro-N,N-bis(trifluoromethyl)prop-1-en-1-amine (935.9 grams, 65.2% purity, 2.2 moles) was produced for a molar yield of 71.1%. The 1,2,3,3,3-pentafluoro-N,N-bis(trifluoromethyl)prop-1-en-1-amine was further purified by fractional distillation to a purity of 99.0%. The structure was confirmed by gc/ms.

1,2,3,3,3-pentafluoro-N,N-bis(trifluoromethyl)prop-1-en-1-amine (159 grams, 99.0% pure, 0.55 moles), 45% aqueous KOH (83.2 grams, 0.67 moles) and Aliquat 336 (1 gram, 2.5 millimoles) were charged to 600 ml stainless steel Parr reactor equipped with stirrer, cooling coil and heating mantle. Methanol (19.6 grams, 0.61 moles) was added in three aliquots to the reactor over a one hour period. The temperature was raised to 50 C, held two hours and then cooled to 35 C and stirred 16 hours. A sample analyzed by gas chromatography showed 37.8% remaining 1,2,3,3,3-pentafluoro-N,N-bis(trifluoromethyl)prop-1-en-1-amine. Acetonitrile (40 grams, 0.97 moles) was added to the reactor and the reactor was stirred at 50 C an additional 16 hours. The reactor was cooled to room temperature and the contents were washed three times with water to provide 1,3,3,3-tetrafluoro-2-methoxy-N,N-bis(trifluoromethyl)prop-1-en-1-amine (122.8 grams, 93.3% pure, 0.39 moles). The material was further purified by fractional distillation to a 99.3% pure mixture of cis and trans isomers. The structure and purity were confirmed by gc/ms and F-NMR. The boiling point is about 78° C.

Other embodiments of the invention are within the scope of the appended claims.

What is claimed is:

1. A working fluid comprising a hydrofluoroether compound represented by the following general formula (II):

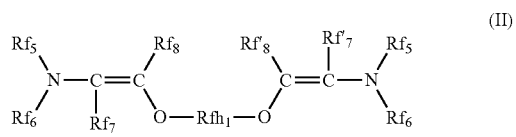

wherein,
$Rf_5$ and $Rf_6$ (i) are each independently perfluoroalkyl groups having 1-8 carbon atoms and optionally comprising at least one catenated heteroatom, or (ii) are bonded together to form a ring structure having 4-8 carbon atoms and optionally comprising one or more catenated heteroatoms;
$Rfh_1$ is a linear, branched, cyclic, or acyclic alkylene or fluoroalkylene group having from 1 to 8 carbon atoms and optionally comprising one or more catenated heteroatoms; and
each of $Rf_7$, $Rf_8$, $Rf'_7$, and $Rf'_8$ is independently a F or $CF_3$ group, with the proviso that when:
$Rf_7$ is F, $Rf_5$ is $CF_3$,
$Rf_8$ is F, $Rf_7$ is $CF_3$,
$Rf'_7$ is F, $Rf'_8$ is $CF_3$, and
$Rf'_8$ is F, $Rf'_7$ is $CF_3$;
wherein the hydrofluoroether compound is present in the working fluid at an amount of at least 50% by weight based on the total weight of the working fluid.

2. An apparatus for heat transfer comprising:
a device; and
a mechanism for transferring heat to or from the device, the mechanism comprising the working fluid according to claim 1.

3. An apparatus for heat transfer according to claim 2, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

4. An apparatus according to claim 2, wherein the mechanism for transferring heat is a component in a system for maintaining a temperature or temperature range of an electronic device.

5. A method of transferring heat comprising:
providing a device; and
transferring heat to or from the device using the working fluid according to claim 1.

* * * * *

UNITED STATES PATENT AND TRADEMARK OFFICE
CERTIFICATE OF CORRECTION

PATENT NO. : 10,385,249 B2
APPLICATION NO. : 16/012811
DATED : August 20, 2019
INVENTOR(S) : Michael Bulinski et al.

Page 1 of 1

It is certified that error appears in the above-identified patent and that said Letters Patent is hereby corrected as shown below:

In the Specification

Column 17, Line 38, After "solvent(s)" insert -- . --.

Column 22, Line 28, Delete "Rf'7," and insert -- Rf'$_7$, --, therefor.

In the Claims

Column 38, Line 25, In Claim 1, delete "Rf$_5$" and insert -- Rf$_8$ --, therefor.

Signed and Sealed this
Twenty-fourth Day of March, 2020

Andrei Iancu
*Director of the United States Patent and Trademark Office*